(12) United States Patent
Reckelhoff

(10) Patent No.: US 8,378,620 B2
(45) Date of Patent: Feb. 19, 2013

(54) SOLAR CHARGED MOBILE WORKING STATIONS

(75) Inventor: Ray Reckelhoff, Elgin, SC (US)

(73) Assignee: Omnicell, Inc., Mountain View, CA (US)

( * ) Notice: Subject to any disclaimer, the term of this patent is extended or adjusted under 35 U.S.C. 154(b) by 383 days.

(21) Appl. No.: 12/438,341

(22) PCT Filed: Aug. 20, 2007

(86) PCT No.: PCT/US2007/076336
§ 371 (c)(1),
(2), (4) Date: Sep. 29, 2010

(87) PCT Pub. No.: WO2008/024722
PCT Pub. Date: Feb. 28, 2008

(65) Prior Publication Data
US 2011/0006724 A1  Jan. 13, 2011

Related U.S. Application Data

(60) Provisional application No. 60/839,104, filed on Aug. 21, 2006.

(51) Int. Cl.
*H01M 10/46* (2006.01)
(52) U.S. Cl. ....................................................... 320/101
(58) Field of Classification Search .................. 320/101, 320/107, 114, 115; 136/243, 244, 245, 291, 136/293
See application file for complete search history.

(56) References Cited

U.S. PATENT DOCUMENTS

| | | | |
|---|---|---|---|
| 4,336,964 A | 6/1982 | Pivar | |
| 4,368,867 A | 1/1983 | Pendleton | |
| 4,372,515 A | 2/1983 | Noonan | |
| 4,471,931 A | 9/1984 | Covey | |
| D279,007 S | 5/1985 | Empson et al. | |
| 4,556,189 A | 12/1985 | Kirpluk | |
| 4,561,620 A | 12/1985 | Goetz | |
| 4,575,033 A | 3/1986 | Henneberg | |
| 4,589,621 A | 5/1986 | Hunt | |
| 4,616,218 A | 10/1986 | Bailey | |
| 4,640,199 A | 2/1987 | Zigman | |
| 4,645,153 A | 2/1987 | Granzow | |
| D289,873 S | 5/1987 | Gemmell et al. | |
| D293,382 S | 12/1987 | Ichikawa | |

(Continued)

FOREIGN PATENT DOCUMENTS

| | | |
|---|---|---|
| CH | 688 607 A5 | 12/1997 |
| DE | 8114991 U1 | 5/1981 |

(Continued)

OTHER PUBLICATIONS

"Korean Makers of TFT-LCD Likely to have Brisk Year", AsiaPulse News, 1 page; Jan. 11, 1999.

(Continued)

*Primary Examiner* — Edward Tso
(74) *Attorney, Agent, or Firm* — Kilpatrick Townsend & Stockton LLP

(57) ABSTRACT

A medical work station having a solar charging system. The medical work station includes a cart that carries a computer for providing access to and keeping track of medical information. The solar charging system is operatively connected to the computer to provide a solar power input. This solar input provides a constant replenishing of power to the computer as long as there is a source of UV light, such as through inside lighting or through sunlight.

20 Claims, 10 Drawing Sheets

U.S. PATENT DOCUMENTS

| | | | |
|---|---|---|---|
| 4,717,112 | A | 1/1988 | Pirkle |
| 4,726,633 | A | 2/1988 | Noble |
| 4,729,533 | A | 3/1988 | Hillary |
| D295,415 | S | 4/1988 | Thies et al. |
| 4,769,634 | A | 9/1988 | Killian |
| 4,834,329 | A | 5/1989 | Delapp |
| 4,836,478 | A | 6/1989 | Sweere |
| 4,836,486 | A | 6/1989 | Vossoughi |
| 4,852,500 | A | 8/1989 | Ryburg et al. |
| 4,918,841 | A | 4/1990 | Turner et al. |
| 4,919,387 | A | 4/1990 | Sampson |
| D310,358 | S | 9/1990 | Nuttall et al. |
| 4,967,928 | A | 11/1990 | Carter |
| D312,630 | S | 12/1990 | Esslinger |
| 4,989,291 | A | 2/1991 | Parent |
| D317,912 | S | 7/1991 | Takai |
| D319,405 | S | 8/1991 | Brawne |
| D319,435 | S | 8/1991 | Brown |
| 5,041,770 | A | 8/1991 | Seiler |
| D326,847 | S | 6/1992 | Savio |
| 5,174,223 | A | 12/1992 | Nagy et al. |
| D337,104 | S | 7/1993 | Orchard |
| D339,796 | S | 9/1993 | Goodner et al. |
| 5,277,392 | A | 1/1994 | Rossman |
| 5,287,815 | A | 2/1994 | Gross |
| D344,933 | S | 3/1994 | Wiseman et al. |
| 5,321,579 | A | 6/1994 | Brown |
| D348,449 | S | 7/1994 | Rodd et al. |
| D349,489 | S | 8/1994 | Wang |
| 5,362,025 | A | 11/1994 | Trom |
| D354,052 | S | 1/1995 | Imai |
| D354,952 | S | 1/1995 | Rodd |
| D357,468 | S | 4/1995 | Rodd |
| 5,437,235 | A | 8/1995 | Randolph |
| 5,442,512 | A | 8/1995 | Bradbury |
| 5,473,997 | A | 12/1995 | Solomon et al. |
| 5,522,323 | A | 6/1996 | Richard |
| 5,536,084 | A | 7/1996 | Curtis et al. |
| D377,720 | S | 2/1997 | Miller et al. |
| 5,630,566 | A | 5/1997 | Case |
| 5,687,717 | A | 11/1997 | Halpern et al. |
| 5,694,199 | A | 12/1997 | Rodriguez |
| D393,382 | S | 4/1998 | Rutter et al. |
| 5,738,316 | A | 4/1998 | Sweere et al. |
| 5,772,637 | A | 6/1998 | Heinzmann et al. |
| 5,775,234 | A | 7/1998 | Solomon et al. |
| 5,806,943 | A | 9/1998 | Dell et al. |
| 5,822,185 | A | 10/1998 | Cavello |
| 5,842,672 | A | 12/1998 | Sweere et al. |
| 5,868,079 | A | 2/1999 | Charny |
| 5,897,179 | A | 4/1999 | Wade |
| 5,918,841 | A | 7/1999 | Sweere |
| 5,960,901 | A | 10/1999 | Hanagan |
| 5,971,341 | A | 10/1999 | Pfister |
| 6,029,580 | A | 2/2000 | Alfonso et al. |
| 6,061,104 | A | 5/2000 | Evanicky et al. |
| 6,085,972 | A | 7/2000 | Wright |
| 6,098,936 | A | 8/2000 | Birrell |
| 6,199,952 | B1 | 3/2001 | Davis |
| 6,269,753 | B1 | 8/2001 | Roddan |
| 6,298,794 | B1 | 10/2001 | Brown et al. |
| 6,394,402 | B2 | 5/2002 | Coonan et al. |
| 6,435,109 | B1 | 8/2002 | Dell et al. |
| 6,493,220 | B1 * | 12/2002 | Clark et al. ............. 361/679.41 |
| 6,721,178 | B1 | 4/2004 | Clark et al. |
| 6,816,145 | B1 | 11/2004 | Evanicky |
| 7,009,840 | B2 | 3/2006 | Clark |
| 8,180,485 | B2 * | 5/2012 | Reckelhoff .................. 700/242 |
| 2001/0004198 | A1 | 6/2001 | Matsuyama |
| 2006/0125356 | A1 * | 6/2006 | Meek et al. .................. 312/215 |

FOREIGN PATENT DOCUMENTS

| | | | |
|---|---|---|---|
| DE | 295 06 433 | U1 | 10/1995 |
| DE | 195 36 664 | A1 | 4/1997 |
| DE | 196 42 425 | A1 | 4/1998 |
| DE | 195 50 100 | A1 | 6/1998 |
| EP | 0 145 410 | | 11/1984 |
| EP | 0 321 137 | | 7/1988 |
| EP | 796575 | A1 | 9/1997 |
| FI | 974408 | A1 | 6/1999 |
| JP | 05-161510 | | 6/1993 |
| JP | 09-262137 | | 10/1997 |
| JP | 10-011172 | | 1/1998 |
| JP | 10-057157 | | 3/1998 |
| JP | 10-146224 | | 6/1998 |
| JP | 11-127976 | | 5/1999 |
| WO | WO 97/46824 | | 12/1997 |

OTHER PUBLICATIONS

24" Wide AnthroCart; http://web.archive.org/web/19970521181347/www.antro.com/hprods_a/p_3.html; (date unknown); p. 1-4.

Advertisement for Ergotron Mobile Work Centers, Integrated Design and Manufacturing; Newsfeed, 1 page, Feb. 1997 issue.

Infoport, The Nursing Station on Wheels; advertisement; www.sculptorsoftware.com/infoport.asp; pp. 1 and 2; visited Mar. 24, 2008.

Anthro Technology Furniture (date unknown); p. 1-40.

Anthro Technology Furniture; New Product Update Fall 1996; (date unknown) pp. 1-12.

Gil Bassak, "Sharp Picture, Fuzzy Forecasting", Electronic Buyers News, p. 44, 3 pages, Jan. 31, 2000.

Ira Goldkang's TRS-80 Revived Site Model 200 Page, www.trs-80/trs80-models-model200.htm, 3 pages, visited Mar. 24, 2008.

Milcare Integrated Storage and Transport Solutions for Health Care; Computer/Storage Cart; Milcare, Inc. (copyright 1997); p. 1-2.

Mobile WorkCenter System; Ergotron; http://www.ergotron.com; (date unknown); p. 1-5.

PCT-SC Ergonomically designed Trans-Mobile self-contained clinical computing workstation system; Tremont Medica brochurel; SC-2/15 (copyright 1997), p. 1-2.

Point-of-Care Cart Systems; MMP MedCart; http://web.archive.org/web/19970301233615/www.medcart.com/pointof.html (date unknown); p. 1-2.

Point-of-Care Carts as part of a Clinical Information System; MMP MedCart; http://www.medcart.com; (date unknown); p. 1-8.

Welcome to Ergotron, retrieved from the Internet on Sep. 17, 2008 at: http://web.archive.org/web/19961104052222/http://www.ergotron.com/; 1 page.

CMS Business; Ergotron (1997); 3 pages.

Ergotron ErgoCart; Ergotron (Rev. 12/97); 2 pages.

Ergotron ErgoLift; Ergotron (Rev. 00-04/99); pp. 1-3.

Evaluation Program; Mobile WorkCenter Solutions; Ergotron; (1997) 5 pages.

Flat Panel Monitor, Keyboard & Laptop; ARMS Product Guide; Ergotron (1994) 8 pages.

MediComp 2001, Options and Accessories; Jaco Mobile Cart Division (1997); 1 page.

MLT 2001; Variable height laptop/peripheral cart; Jaco Mobile Cart Division (1997); 3 pages.

Mobile WorkCenters, Featuring Ergotron's Patented Monitor Suspension System; Ergotron; (1994) 4 pages.

The Ergotron ErgoCart, A Mobile and height adjustable solution for an entire computer system; Ergotron (1999); 2 pages.

The Ergotron ErgoCart, A Mobile solution for an entire computer system; Ergotron (1998); 2 pages.

All the Right Moves . . . Flat Panel Monitor Mounting Solutions; Ergotron; (1997); 4 pages.

European Supplemental Search Report of European Application Number 07 81 4264 mailed on Oct. 19, 2012, 17 pages.

* cited by examiner

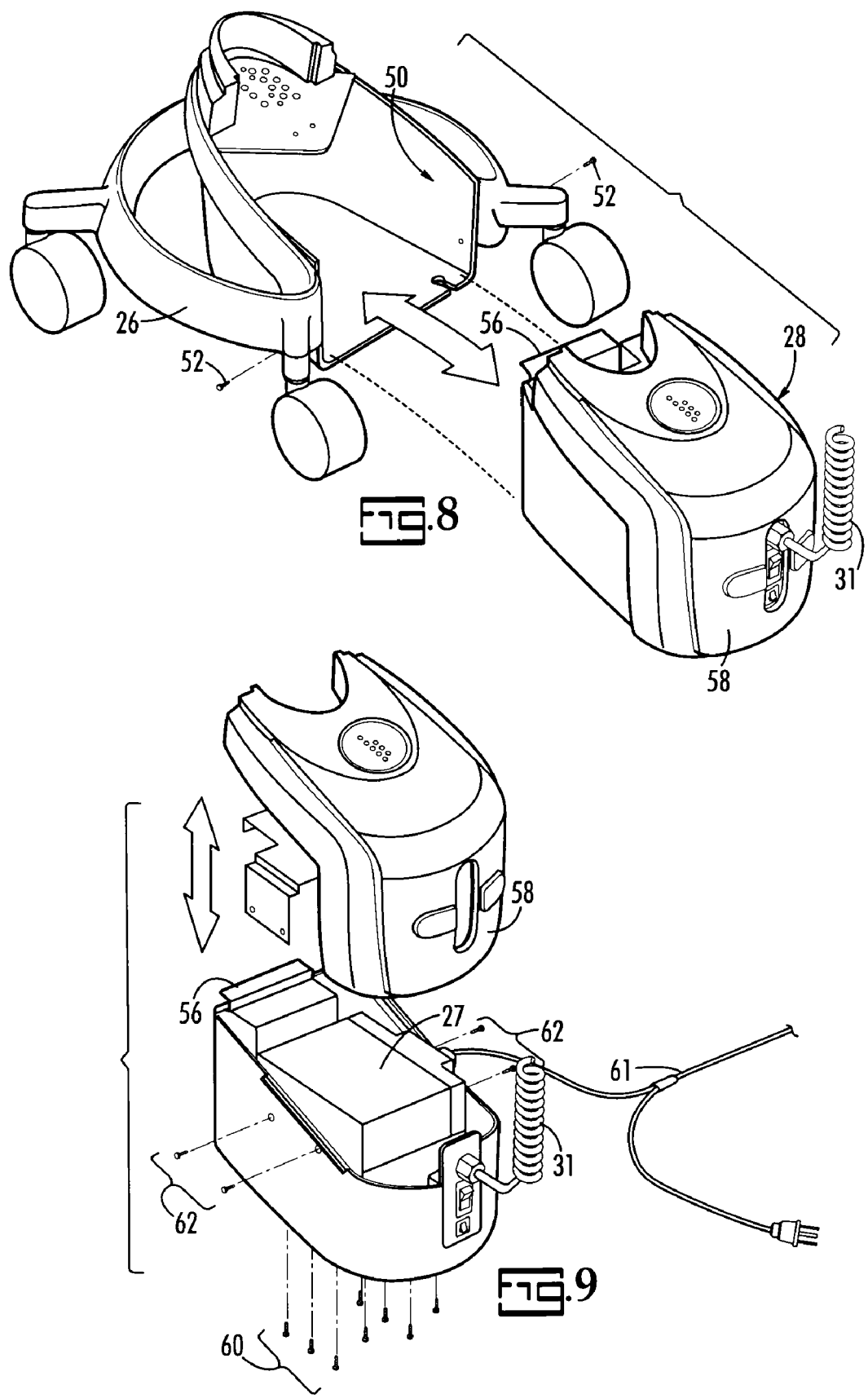

SOLAR CHARGED MOBILE WORKING STATIONS

BACKGROUND OF THE INVENTION

The present invention relates to solar charging systems, and, in particular, for a solar charging system for mobile work stations.

As with many other industries, the health care industry strives to provide quick and convenient access to as much useful information as possible to those in need of it. Timely and consistent access to accurate information is especially significant, however, when considering that the health and lives of others are at stake.

The use of wireless computers, therefore, has had a tremendous impact on the effectiveness and efficiency of medicine. The more mobile a healthcare professional or employee can be the better chance that a patient can receive prompt and accurate care. Accordingly, there exist wireless work stations having computers that provide such information as medication charts and patient records, and that have e-mail capabilities so that the information can be shared. These work stations can further include features that enable the proper administration of medication.

Although these types of work stations are advantageous in their convenience and capabilities, they can prove to be expensive. Thus, extending the life of the work stations is desirable. Furthermore, the work stations require a significant amount of power that frequently needs recharging.

Accordingly, there exists a need for a durable work station that can be operated without constant or frequent replenishing of power.

SUMMARY OF THE INVENTION

The following presents a simplified summary of the invention in order to provide a basic understanding of some aspects of the invention. This summary is not an extensive overview of the invention. It is not intended to identify key or critical elements of the invention or to delineate the scope of the invention. Its sole purpose is to present some concepts of the invention in a simplified form as a prelude to the more detailed description that is presented later.

According to its major aspects and briefly recited, the present invention is a medical work station having a solar charging system. The medical work station includes a cart that carries a computer for providing access to and keeping track of medical information. The solar charging system is operatively connected to the computer to provide a solar power input. This solar input provides a constant replenishing of power to the computer as long as there is a source of UV light, such as through artificial and natural light.

In particular, the computer includes wireless network access and a monitor. Preferably, the monitor includes an LCD screen that draws less power than standard LCD screens currently available. For example, the LCD screen draws less than about 2 Amps of power.

An important feature of the present invention is the use of a solar charging system in combination with a medical work station. The use of a solar charging system provides enhanced mobility to the work station, which no longer needs to be plugged into a power source. Additionally, the solar charging system extends the life of the work station as its power is constantly replenished by solar input.

Another important feature to the present invention includes the use of medical work station having a computer with an LCD screen that draws a certain amount of power so as to provide an overall power reduction to the computer. In particular, the LCD screen draws less than about 2 Amps of power, so that the computer requires less power input to operate.

Yet another feature of the present invention includes the use of a medical work station having a computer with an LCD screen and a solar charging system that work in combination to enhance the efficiency and extend the life of the medical work station. With less overall power required to operate the computer, the computer's solar charging system functions all the more efficiently, as it will require less overall solar input to charge the computer Another feature of the present invention is based on the recognition that the environment of use is a medical facility where there is ample lighting particularly, when a cart is in use. The recognition of this fact of that environment in combination with the use of a solar panel to charge the cart's battery and that can take advantage of the bright lights in that environment allows the cart to be operated without having to recharge the batteries by other means.

These and other features and their advantages will be apparent to those skilled in the art of dispensing medications to patients from a careful reading of the Detailed Description of Preferred Embodiments accompanied by the following drawings. The present invention relates to dispensing medication to patients in hospitals and nursing homes

BRIEF DESCRIPTION OF THE SEVERAL VIEWS OF THE DRAWINGS

In the drawings,

FIG. 8 is a detailed, exploded, perspective view of the base of a medication dispensing cart, showing the battery in its cover being separated from the battery bracket on the base, according to an alternative embodiment of the present invention;

FIG. 9 is a detailed, exploded, perspective view of the battery cover showing the battery inside, according to an alternative embodiment of the present invention;

DETAILED DESCRIPTION OF THE INVENTION

Figure 1:
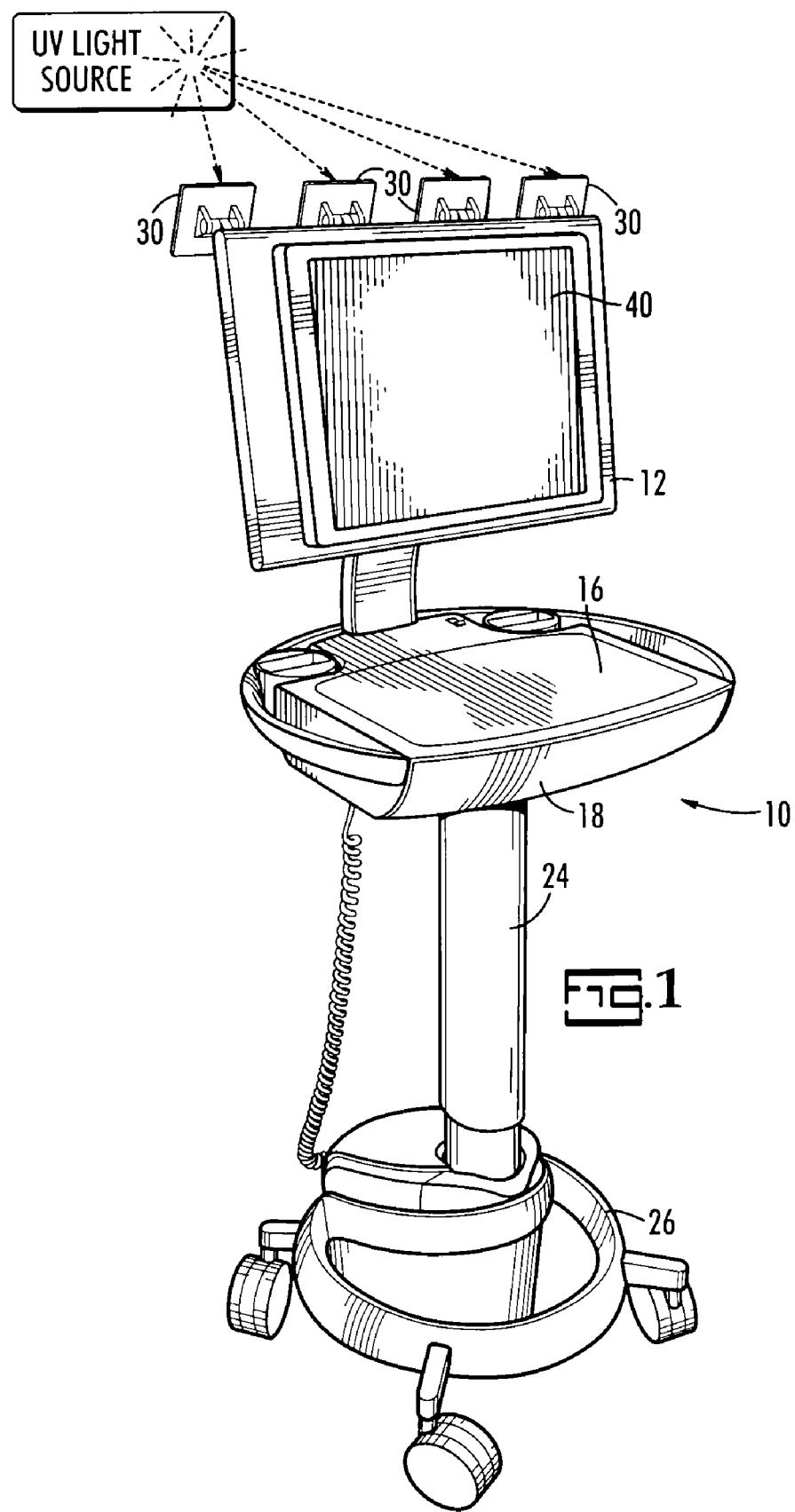
FIG. 1 is a perspective illustration of a medical work station, according to a preferred embodiment of the present invention.
Figure 2:
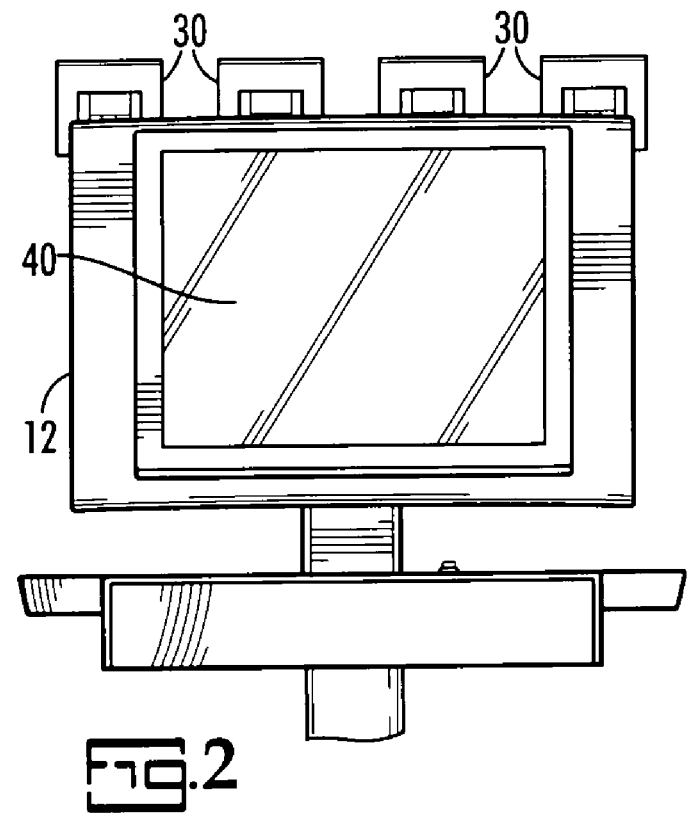
FIG. 2 is a front, perspective view of a medical work station according to a preferred embodiment of the present invention.
Figure 3:
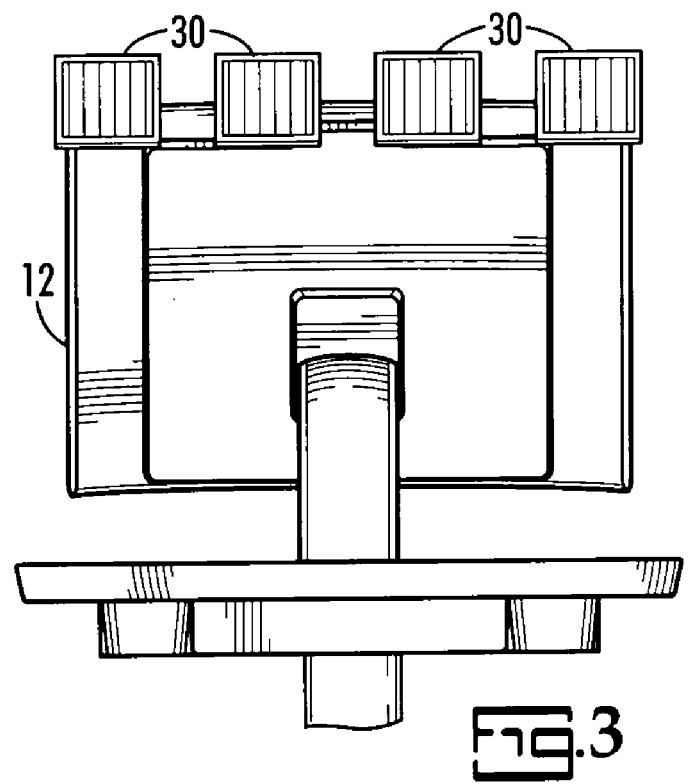
FIG. 3 is a rear, perspective view of a medical work station according to a preferred embodiment of the present invention.
Figure 4:
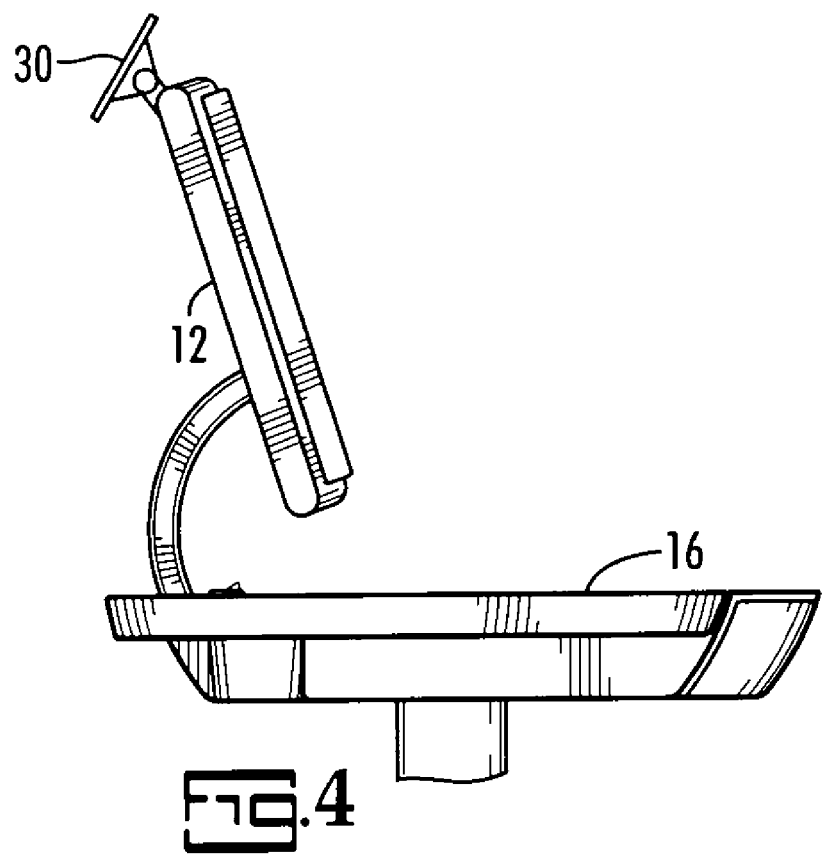
FIG. 4 is a side, perspective view of a medical work station according to a preferred embodiment of the present invention.
Figure 5:
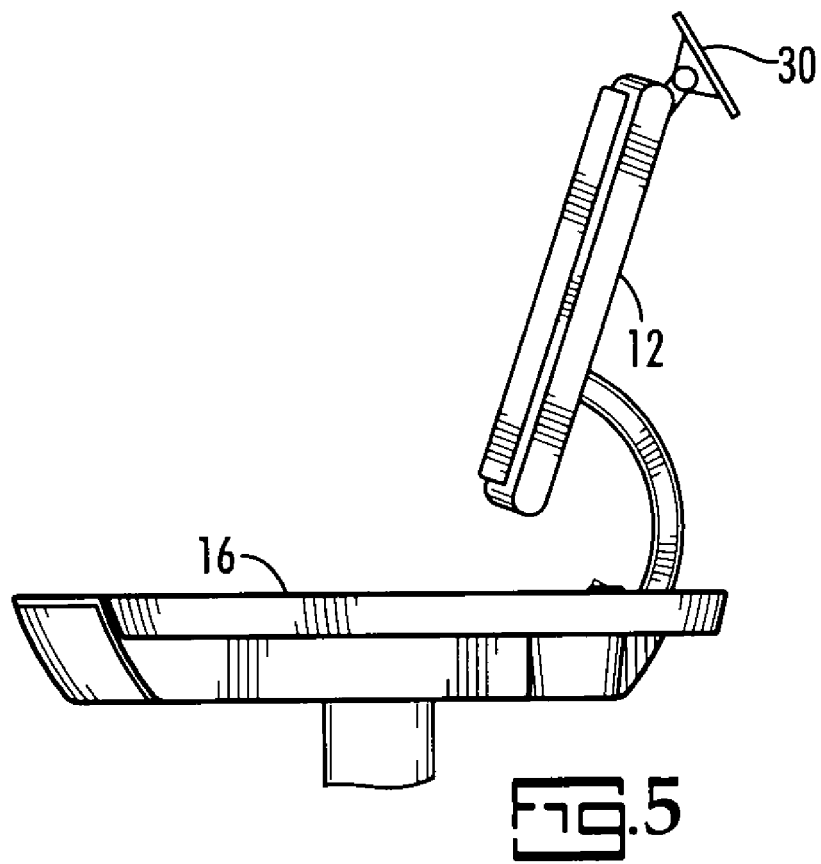
FIG. 5 is a side, perspective view of a medical work station according to a preferred embodiment of the present invention.

The present invention is a medical work station having a solar charging system. As shown in FIGS. 1-5, the medical work station includes a cart that carries a computer for providing access to and keeping track of medical information. The cart, as generally indicated in FIG. 1 by reference number 10, includes a variety of features and embodiments. Accordingly, the cart shown in FIG. 1 is merely exemplary and provided to place the present invention into context. Generally, cart 10 includes a computer/monitor 12, preferably with both a computer and a monitor in one unit with the computer behind the monitor and in the same housing. Computer/monitor 12 is equipped with a wireless network connection so that the user of that cart 10 can communicate with a central administrator. Computer/monitor 12 also communicates with administrator without the active assistance of the user. Cart 10 also has a work surface 16 with a slide out keyboard 18. Additionally, surface 16 is mounted on top of a mast 24 carried in turn by a rolling base 26.

The solar charging system of the present invention is operatively connected to the computer/monitor 12 to provide a solar power input. This solar input provides a constant replenishing of power to the computer as long as there is a source of UV light, such as through inside lighting or through sunlight. For example and as illustrated, the solar charging system includes a plurality of solar panels 30 that are connected to the computer/monitor 12. This solar input provides a constant replenishing of power to the computer as long as there is a source of UV light, such as through inside lighting or through sunlight. As illustrated, the solar panels 30 are located near the top of computer/monitor 12 and facing away from the user of the computer/monitor 12.

Optionally, the solar panels 30 are rotatably connected to the computer/monitor 12 so that they can be ideally positioned for receiving a source of UV light. Additionally, the solar panels 30 can be releasably connected to the computer/monitor 12 so that they can be both rotated and moved to optimum locations.

This configuration can be altered based on the conditions of a medical center and the length of the duty cycle. For example, a cart used in an emergency room where lighting is brighter around the clock as opposed to, say, a maternity ward, there may be sufficient lighting for a longer duty cycle and a smaller solar panel. A long term care facility may have even lower levels of lighting and shorter duty cycles. A reasonable amount of experimentation by those skilled at matching solar panel design with environment and duty cycle is required to optimize the panel design for the particular environment.

Although amounts of power generated may vary according to the amount of a size of the solar panels 30, the solar charging system of the present invention generates about 1 Amp of power indoors without input from natural light, and about 2 to about 3 Amps of power with the input of natural light. Preferably, the computer/monitor 12 of the workstation should not need recharging if it is operated at less than about 50% duty time.

As discussed, an important feature of the present invention is the use of a solar charging system in combination with a medical work station. The use of a solar charging system provides enhanced mobility to the work station, which no longer needs to be plugged into a power source. Additionally, the solar charging system extends the life of the work station as its power is constantly replenished by solar input.

Computer/monitor 12 of the present invention further includes an LCD screen 40 that draws less power than prior art monitors by such means as, for example, keeping the monitor at a modest size, reducing brightness but compensating by increasing contrast. Another important feature to the present invention includes the use of medical work station having a computer with an LCD screen 40 that draws a certain amount of power so as to provide an overall power reduction to the computer. In particular, the LCD screen 40 draws less than about 2 Amps of power, so that the computer requires less power input to operate. Moreover, the LCD screen 40 and solar charging system works in combination to enhance the efficiency and extend the life of the medical work station. With less overall power required to operate the computer, the computer's solar charging system functions all the more efficiently, as it will require less overall solar input to charge the computer.

As discussed, the present invention can be employed with any number of types of medical. An example of a medical cart that can be used in combination with the solar power system is now described.

Figure 6:
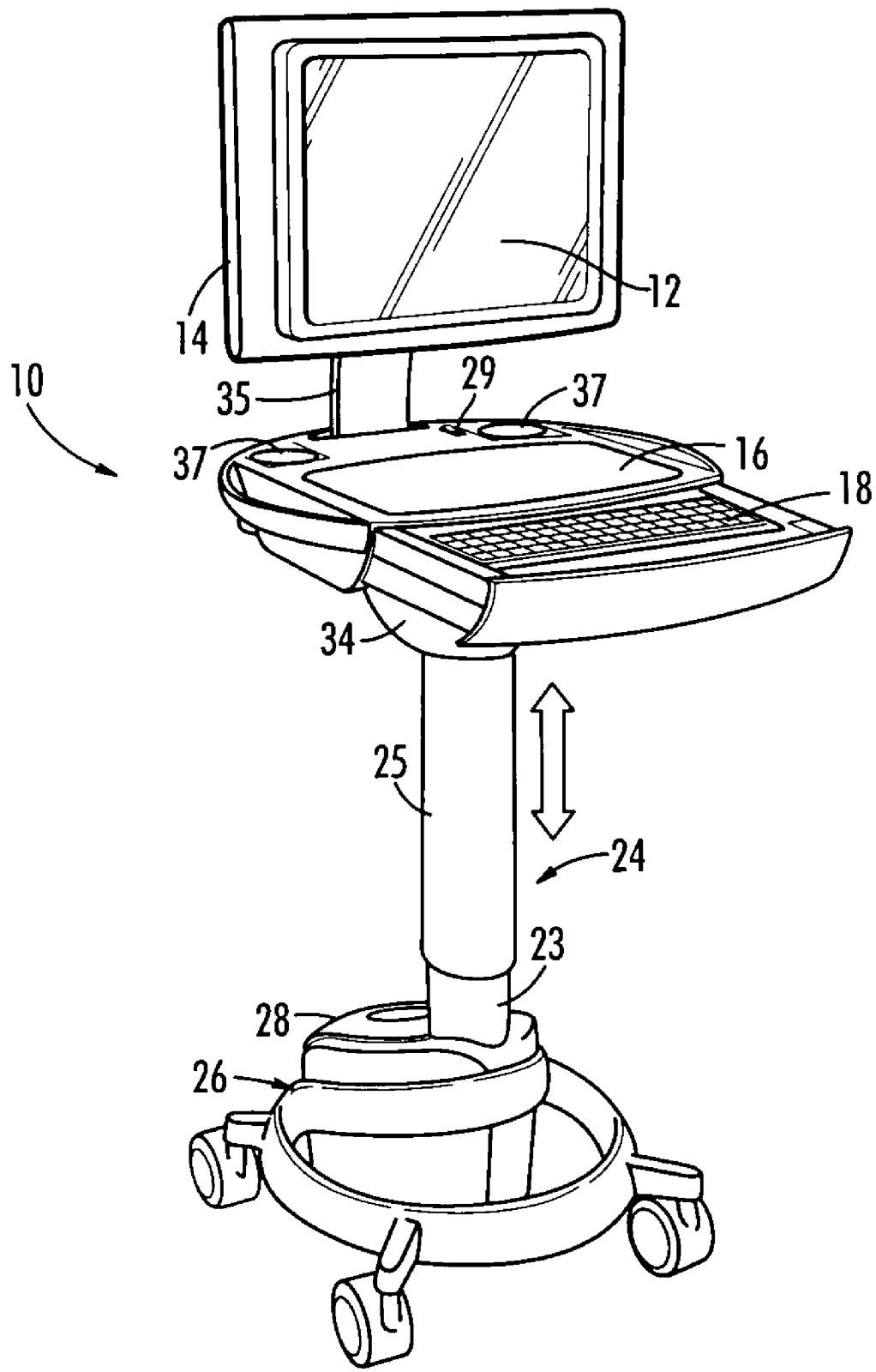
FIG. 6 is a perspective illustration of a medication dispensing cart, according to an alternative embodiment of the present invention.

An exemplary cart is shown generally in FIG. 6 by reference number 10. The cart includes a computer/monitor 12, preferably with both a computer and a monitor in one unit with the computer behind the monitor and in the same housing 14. Cart 10 also has a work surface 16 with a slide out keyboard 18. There is no security keypad; the keyboard's keypad serves for entry of codes to permit access. Work surface 16 is mounted on top of a mast 24 carried in turn by a rolling base 26. Work surface 16 can optionally include holders for storing items, such as antibacterial lotions and drinks, which the user may need when making rounds with the cart 10.

Figure 7:
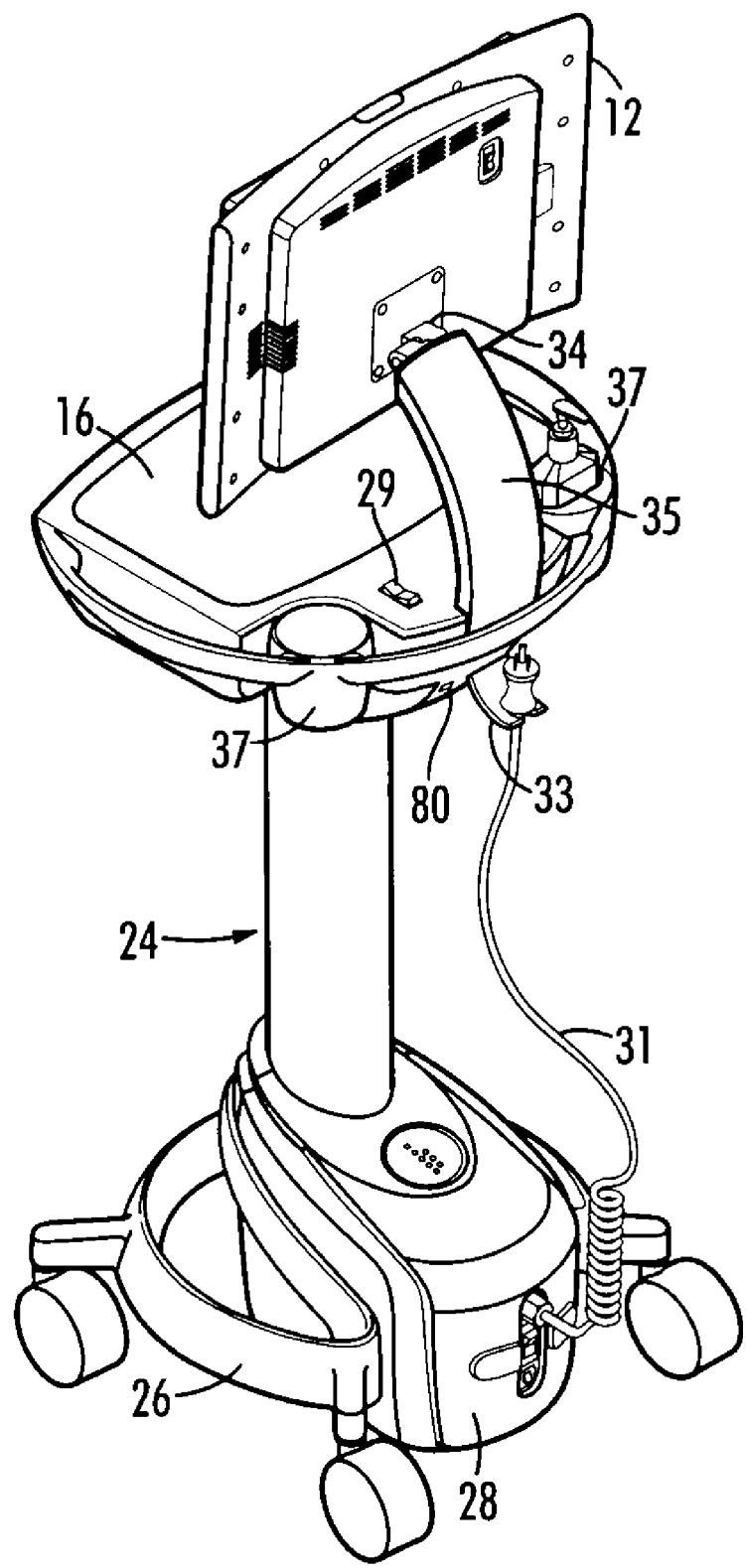
FIG. 7 illustrates a rear, perspective view of a medication dispensing cart according to an alternative embodiment of the present invention.

Referring to FIG. 7, there is illustrated a rear view of the present cart 10 showing computer/monitor 12, work surface 16, mast 24, and a power system 28, which is carried by rolling base 26. Work surface 16 can further include hidden USB port 80 for use if additional electronic devices, such as scanners, need to be employed. Computer/monitor 12 is attached to mast 24 or underneath the work surface through a mount 35 so that the entire top area of the work surface 16 is available to the user. Computer/monitor 12 is mounted using a tiltable bracket 34 so that the angle of viewing computer/monitor 12 can be adjusted to suit the particular user. A clear hard covering is applied over the monitor portion of computer/monitor 12 in order to make computer/monitor less susceptible to scratches and impact. Preferably the covering is about a ⅛th inch thick and made of acrylic polymeric plastic or other suitable plastic polymer.

Mast 24 is vertically adjustable so that the user can work seated or standing and users of different heights can work comfortably. Preferably, mast 24 is electronically adjustable by pressing a button 29 rather than by turning a hand crank or other mechanical elevating mechanism. As shown in FIG. 6, the mast 24 is telescoped, with an outer mast member 25 dimensioned to receive an inner mast member 23. This arrangement enables the raising and lowering of the computer/monitor 12 and work surface 16. The raising and lowering of the mast 24 can be controlled by an electrical switch 29 that is connected to the power system 28 and mechanical means (not shown), such as a screw/nut drive system that utilizes a number of small balls (ball screw). In operation, a user would press the button 29 in one direction, such as forward, to activate the electrical switch 29 to lower the mast 24, and in another direction, such as backward, to activate the electrical switch 29 to raise the mast 24. The electrical switch 29 provides input to the power system 28, which controls the raising and lowering of the mast 24 through an actuator connected to the mechanical means. Alternatively, the power system can also include a weight sensor connected to the actuator that can be used to override the raising and lowering of mast 24 based on the weight of the work surface 16 and computer/monitor 12. For example, if the combined weight of the work surface 16 and computer/monitor 12 exceeds a preset, desired weight, the actuator will be tripped, and the mast 24 will no longer be moveable through the use of the button 29.

An alternative power system 28 is illustrated in further detail in FIGS. 8-9. If solar input is insufficient to power the medical cart, the power system 28 can provide an alternative source of power as needed to ensure the constant operation of the medical cart. As shown, power system 28, which is connected through mast 24 to computer/monitor 12, includes a power system controller (not shown) and a battery 27 that is carried in a battery bracket 50 held in rolling base 26. As discussed, the battery 27 can be charged in combination with the cart 10 or independently of the cart 10, through a power cord 31. Thus, work surface 16 further includes a power cord 31 plug rest 33 (shown in FIG. 7) for conveniently storing the power cord 31 when the cart 10 is being moved or is not in the vicinity of a power source. Battery 27 can be fixed to battery bracket 50 with a variety of mechanical fasteners. In a preferred embodiment, battery 27 is fixed to battery bracket by two screws 52. By removing screws 52, battery 27 and its associated electronics can be removed from bracket 50 to expose the wiring connections. Once the wiring connections are disconnected, battery 27 can be lifted free using its handle 56. Battery 24 is still in a cover 58 and may remain in cover 58 during recharging.

In the event battery 27 needs to be replaced altogether, the screws 60 holding battery 27 in its cover 58 are removed, then the battery hold down screws 62 are removed and finally, battery 27 can be disconnected and replaced. It will be clear that having both a battery cover 58 that stays with battery 27 while battery 27 is either in service or being recharged, and which battery 27 and cover 58 can be quickly removed from cart 10, makes it faster and easier to keep fully charged batteries on carts 10.

As discussed, battery 27 can be charged in combination with the cart 10 or independently of the cart 10, through a power cord 31. Thus, work surface 16 further includes a power cord 31 plug rest 33 for conveniently storing the power cord 31 when the cart 10 is being moved or is not in the vicinity of a power source. Additionally, power system 28 can be equipped with an LED indicator to show when the batter 27 is charging and/or fully charged.

Battery 27 is designed to last through at least one shift of eight hours before requiring recharging, preferably about 10 hours. In addition, each battery is connected to the balance of cart 10 using a "Y" electrical connector 61 that permits a second, fully charged battery 27 to be connected (for "hot swapping") to the unused part of the Y connector, and then the first battery 28 can be removed from the battery bracket and disconnected from the Y connector without loss of power, or data, to computer/monitor 12, and the second battery can then be installed into the battery bracket. The connections that hold battery 28 in its bracket are designed for quick release so battery change out takes but a few minutes at most.

Figure 10:
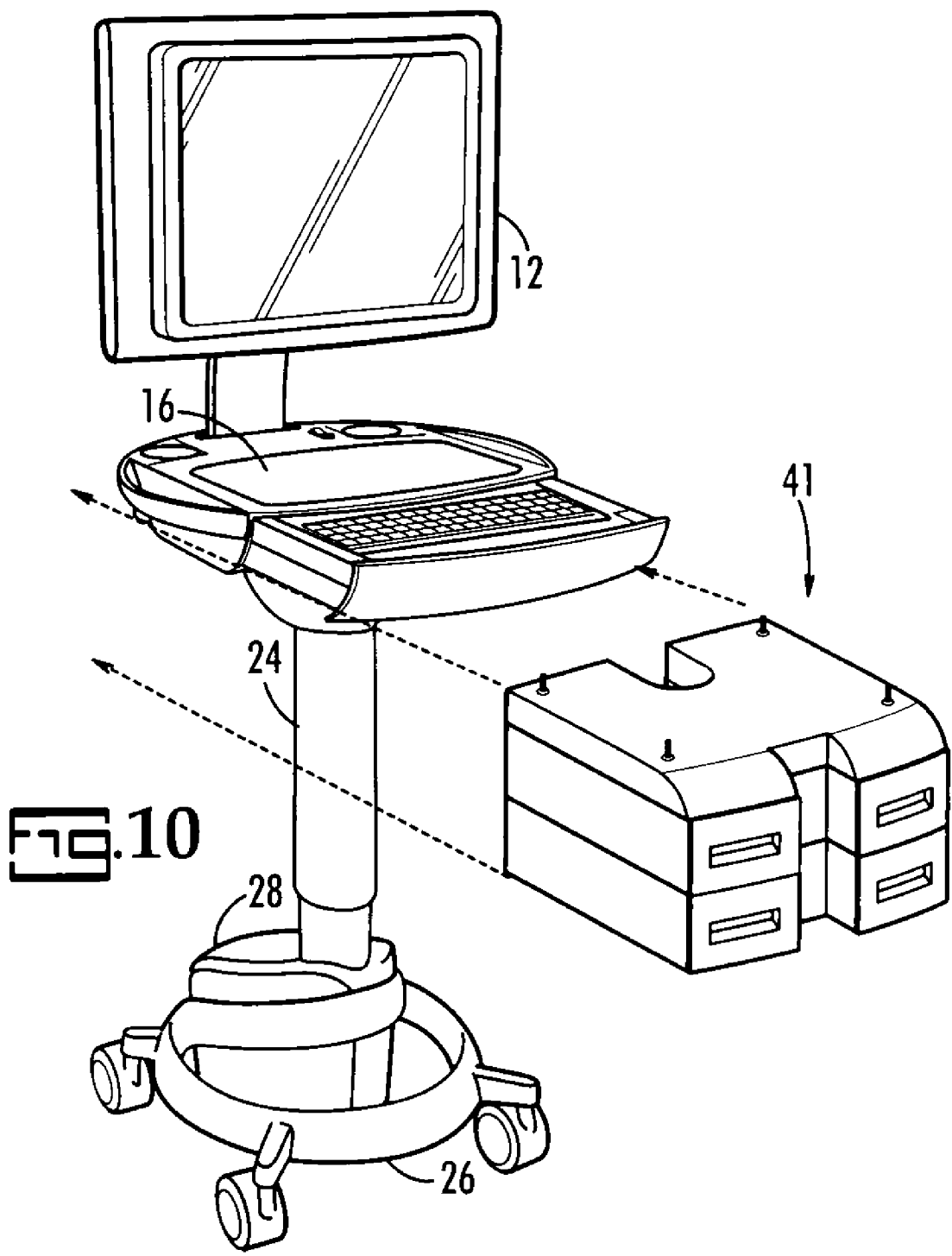
FIG. 10 is a perspective, partially exploded view of the medication cart of FIG. 1 showing the cassette drawer system in relation to the cart itself, according to an alternative embodiment of the present invention.
Figure 11:
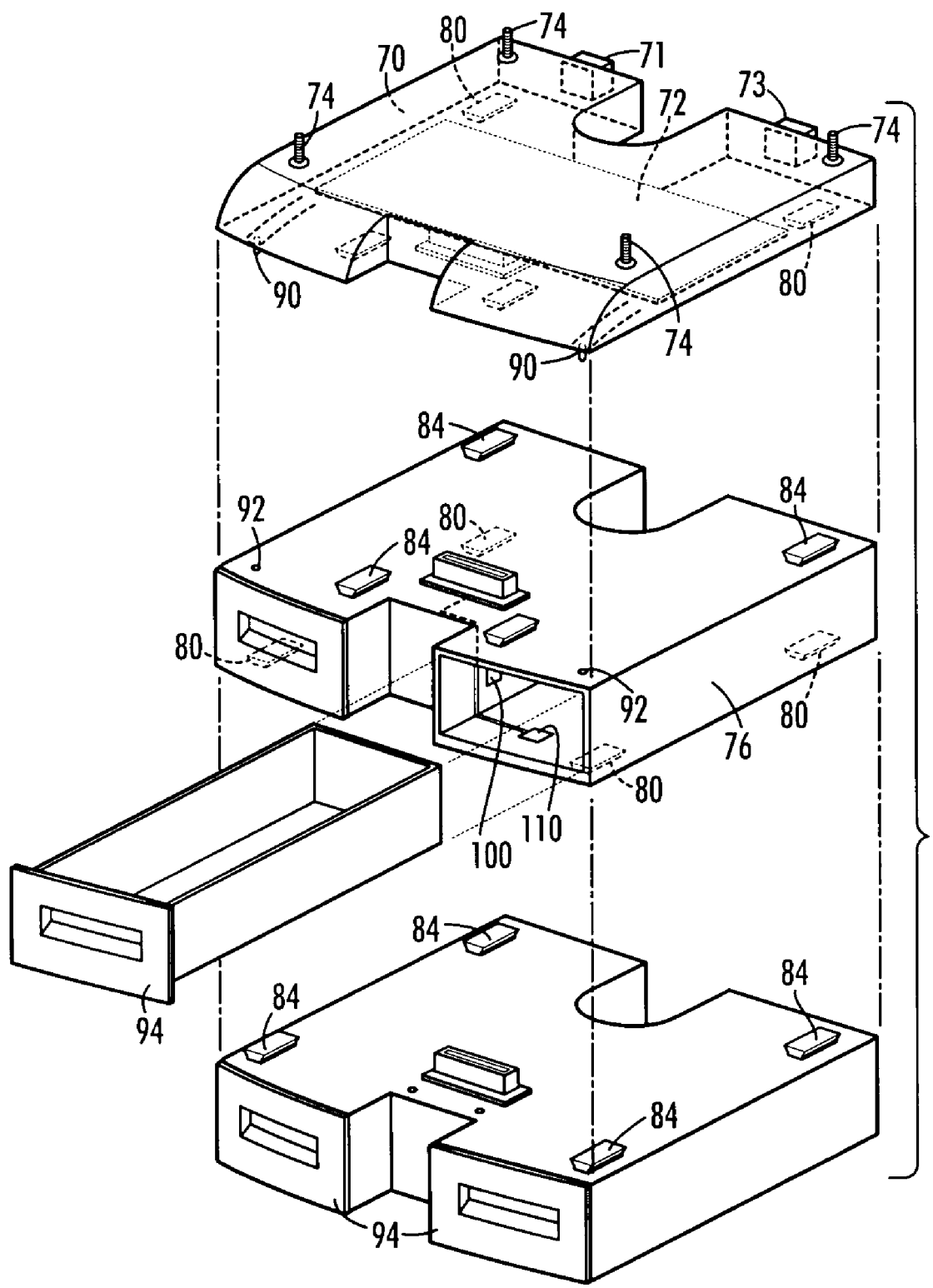
FIG. 11 is a perspective, detailed exploded view with two expanded detailed drawings of the cassette drawer arrangement, according to an alternative embodiment of the present invention.

Referring now to FIG. 10, cart 10 preferably includes a cassette drawer system 41. As illustrated, at least one cassette drawer system 41 can be carried below work surface 16. An exploded, detailed view of the cassette drawer system 41 is shown in FIG. 11. Cassette drawer system 41 is preferably modularized, and includes a cassette drawer manager 70, which houses a cassette drawer controller and interface 72 for monitoring the status and activities of cassette drawers and receiving input for computer/monitor 12. The cassette drawer system 41 is generally connected to work surface 16 and wired to computer/monitor 12. More particularly, the top of cassette drawer manager 70 is bolted to work surface 16. Accordingly, cassette drawer manager 70 includes bolt fasteners 74 along its top surface. Optionally, cassette drawer manager 70 includes a first key override lock 71 and a second key override lock 73. In the event drawers need to be opened, and the cassette drawer system 41 or the computer/monitor 12 system is malfunctioning, a first key from authorized users will override the cassette drawer manager controller 72 to open the drawers containing certain medication. If narcotic medication needs to be accessed, a user must insert both a first key and a second key to open the narcotics-containing drawers.

Beneath cassette drawer manager 70, at least one cassette drawer 76 is latched. Depending on the dimensions of the cassette drawer manager 70 and the cassette drawers, up to four drawers 76 can be added. An added drawer 76 cannot be released without opening the drawer. As soon as a drawer 76 is added, it is sensed by controller of computer/monitor 12 and cannot be opened except by a user with an authorizing pass code.

The latching mechanism between the cassette drawer manager 70 and a cassette drawer 76 will be the same as between a first cassette drawer and a second cassette drawer. This latching mechanism is shown in the expanded detailed drawings in FIG. 11. As between the cassette drawer manger 70 and a first cassette drawer, on the underside of cassette drawer manager 70 are a plurality of dovetail-shaped cutout portions 80 that are dimensioned to receive dovetail-shaped projections 84. Similarly, on the underside of each cassette drawer 76 are a plurality of dovetail-shaped cutout portions 80 that are dimensioned to receive dovetail-shaped projections 84 on every lower cassette drawer 78. In operation, dovetail projections 84 simply slide into dovetail cutouts 80.

Once cassette drawer 76 is seated fully into cassette drawer manager 70, spring tabs 90 having pins 91, which have been cut out from the bottom surface of cassette drawer manager 70, are cammed upward as drawer 76 is slid into place, and snap downward into corresponding recesses 92 in the top surface of drawer 76. Pins 91 on spring tabs 90 will hold drawer 76 in place until drawer 76 is opened by an authorized person who can then pull tabs 90 down to release drawer 76 from manager 70. Preferably, once cassette drawer manager 70 and any and all additional cassettes are in place, the cassette drawer manager 70 and the cassette drawers are also electronically connected.

As illustrated, cassette drawer manager 70 and cassette drawer 76 are generally U-shaped to facilitate engagement with the mast 24. Each cassette drawer 76 typically has at least two compartments 94 that are independently lockable through electronic locks 100 and that have corresponding sensors 110. Sensors 110 determine if a drawer is open or closed, including of course when a drawer is left open or not fully closed. A drawer that is opened without authorization causes an alarm to sound and initiates an email to the system administrator. All locks 100 are software controlled rather than by using keys. For example, a lock 100 could include a solenoid actuator connected to a lever and controlled by software. Keys can be lost or stolen or fall into the wrong hands. Furthermore, it is easier to change access pass codes using software than to re-key locks. Computer/monitor 12 can be programmed to lock every drawer unless unlocked by a person with the correct level of authorization who enters the correct pass code via keyboard 18. Access to a compartment 94 containing narcotics requires two pass codes; otherwise one pass code unlocks a compartment 94. Each user has his or her own pass code or codes so the user who accesses each drawer is known by the pass code used, as well as the time and date of the access by that user.

Cart 10 is optionally provided with a plug in scanner for reading medication containers and automatically and accurately loading drawers and the computer database with the correct information about the medications being loaded into each drawer. In this way, the system administrator can have a real time inventory of medications in all carts in its system, knowing exactly what type and how much medication is in each drawer of each cart Cassette drawer system 41 also has an optional utility cassette 78, which can be used to store such items as rubber gloves, paper cups, tissues, and so forth. Because a utility cassette 78 need not be secured, cassette drawer manager 70 automatically deactivates sensors 110 and locks 100 of utility cassette drawers 78 that become part of the cassette drawer system 30.

Figure 12:
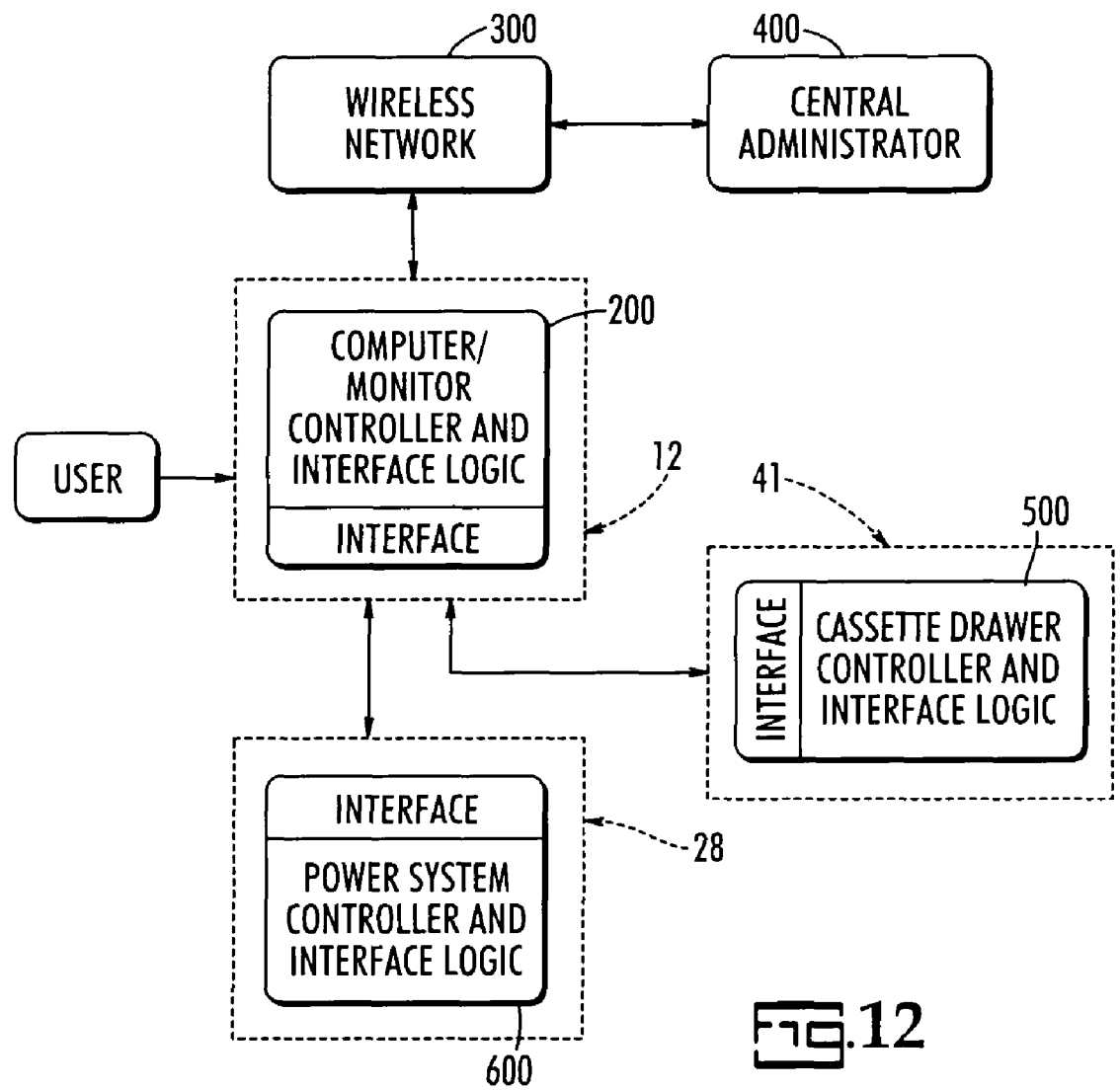
FIG. 12 is a block diagram of various components of the medication cart system, according to an alternative embodiment of the present invention.

A block diagram of the operating system for the cart 10 is shown in FIG. 12. As illustrated, computer/monitor 12 includes a computer controller and interface logic 200 that receives computer controller input and generates computer controller output. For example, computer controller 200 process user input, such as the identity of user, the biometric information of user, pass codes entered by user. Furthermore, computer controller provides output to cassette drawer system 41 relating to the designation of cassette drawers included in the cassette drawer system 41. Significantly, computer/monitor 12 can, in real time, inventory medication as it is loaded and as it used, as well as which user is dispensing the medication. Additionally, computer/monitor 12 is equipped with a wireless network connection, preferably through SMTP (simple mail transfer protocol) so that the user of that cart 10 can communicate with a central administrator 400. Computer/monitor 12 also communicates with administrator 400 without the active assistance of the user. Accordingly, the status and whereabouts of the cart 10 can be constantly and effectively monitored through wireless communication.

Figure 13:
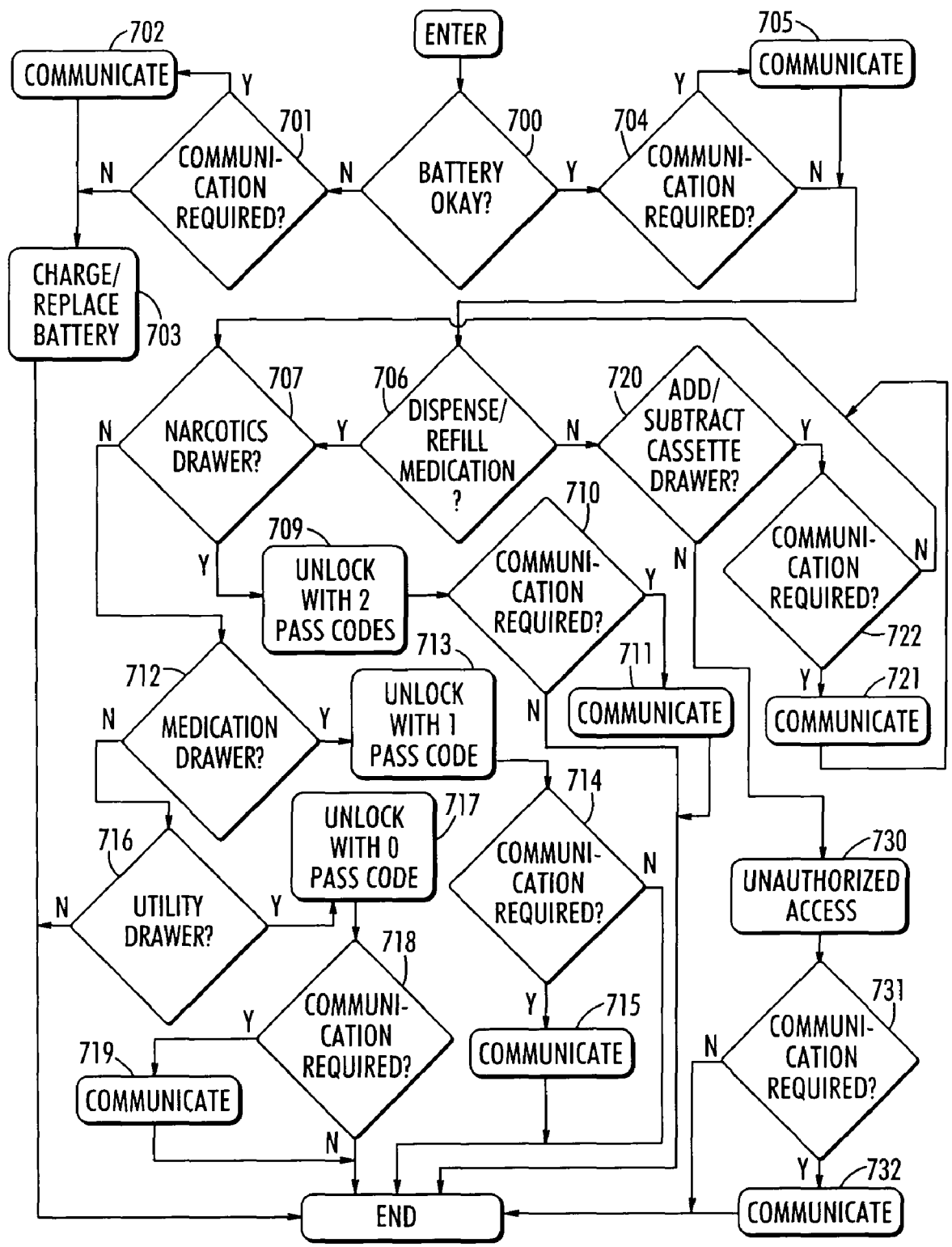
FIG. 13 is a logic flow chart of various components of the medication cart system, according to an alternative embodiment of the present invention.

As previously described, the cassette drawer system 41 also includes cassette drawer controller and interface logic 500. This cassette drawer controller receives input from the computer controller about the cassette drawers and their designations. Cassette drawer controller, therefore, can lock and unlock drawers based on this input. Furthermore, the cassette drawer controller logs what the drawers do, including when they are opened and by whom. Accordingly, the cassette drawer system 41 has the ability to monitor itself. Similarly, the power system 28 also includes controller and interface logic 600, which monitors the condition of battery 27, and controls the raising and lowering of the mast 24. For example, the condition of the battery 27 when low or when the unit is turning off due to low battery power, power system controller communicates these conditions to computer controller, which in turn reports by email to the administrator. Computer/monitor 12 will also automatically report by email an attempt to break into cart 10, a log of the charging system, a log of the times and the identities of users who have accessed each cassette drawer. Other information can also be reported To summarize an embodiment of the logic for the medication cart system, FIG. 13 includes of flow chart. As shown, at 700, a decision is made by medication cart 10 whether the battery 27 is suitable. If the battery 27 is not in a good condition and if communication is required at 701 as to the status of the battery 27, an electronic communication is sent to central administrator at 702. If maintenance is needed, the battery 27 will be charged or replaced at 703. If the battery 27 is in good condition and communication is required at 704, an electronic communication is sent to central administrator at 705.

At 706, a decision is made as to whether medication must be dispensed or refilled. If narcotic medication must be dispensed or refilled at 707, the narcotics drawer is unlocked with two pass codes at 709. If communication as to the status of the narcotics drawer is required at 710, an electronic communication is sent to central administrator at 711. If non-narcotic medication must be dispensing or refilling at 712, the medication drawer is unlocked with on pass code at 713. If communication as to the status of the medication drawer is required at 714, an electronic communication is sent to central administrator at 715. If a utility drawer needs to be accessed at 716, the utility drawer is unlocked with no need for a pass code at 717. If communication as to the status of the utility drawer is required at 718, an electronic communication is sent to central administrator at 719.

If user adds or subtracts a cassette drawer from the cassette drawer system 41 at 720 and communication is required as to the status of the cassette drawer system 41 at 721, an electronic communication is sent to central administrator at 722. If, on the other hand, an unauthorized access to the cassette drawer system 41 is attempted or accomplished at 730, and communication is required as to the status of the cassette drawer system 41 at 731, an electronic communication is sent to central administrator at 732.

It is intended that the scope of the present invention include all modifications that incorporate its principal design features, and that the scope and limitations of the present invention are to be determined by the scope of the appended claims and their equivalents. It also should be understood, therefore, that the inventive concepts herein described are interchangeable and/or they is used together in still other permutations of the present invention, and that other modifications and substitutions will be apparent to those skilled in the art from the foregoing description of the preferred embodiments without departing from the spirit or scope of the present invention.

What is claimed is:

1. A system, comprising:
    a medical work station including a cart having a computer and a battery, wherein said computer includes a display screen, wherein the cart further comprises a base having a plurality of wheels coupled thereto, a mast extending generally vertically up from the base, a work surface operably coupled to the mast and a drawer system disposed below the work surface and at least partially about the mast, and wherein the battery is included within the base; and
    a solar charging system that is operatively connected to said medical work station, wherein said solar charging system has a solar power input that provides a constant replenishing of power to said computer as long as there is a source of UV light.

2. The system as recited in claim 1, further comprising a central administrator that is operatively connected to said computer.

3. The system as recited in claim 2, wherein said computer has wireless network connection for communicating with said central administrator.

4. The system as recited in claim 3, wherein said computer communicates with said central administrator without the active assistance of the user.

5. The system as recited in claim 1, wherein said solar charging system includes a plurality of solar panels that are connected to said computer.

6. The system as recited in claim 5, wherein each of said plurality of solar panels is rotatably connected to said computer.

7. The system as recited in claim 5, wherein each of said plurality of solar panels is releasably connected to said computer.

8. The system as recited in claim 1, wherein said solar charging system generates about 1 Amp of power indoors without input from natural light.

9. The system as recited in claim 1, wherein said solar charging system generates about 2 to about 3 Amps of power with the input of natural light.

10. The system as recited in claim 1, wherein said solar charging system generates sufficient power to avoid recharging said computer if it is operated at less than about 50% duty time.

11. The system as recited in claim 1, wherein said display screen draws less than about 2 Amps of power.

12. A system comprising:
a base defining a battery slot;
a mast extending generally vertically up from the base;
a work surface operably coupled to the mast;
a computer comprising a controller; and
a computer monitor that is operably coupled to the controller, wherein the computer monitor is operably coupled to the mast so as to be positioned above the work surface;
a drawer system disposed between the work surface and the base;
a battery removably positioned within the battery slot, wherein the battery comprises a housing and a handle coupled to the housing to facilitate removal and replacement of the battery; and
a solar charging system that has a solar power input that provides power to operate the computer.

13. A cart as in claim 12, wherein the battery is configured to be recharged while in the battery slot or when removed from the cart using a separate charger.

14. A cart as in claim 12, wherein the drawer system comprises a first drawer housing that is configured to be removably coupled beneath the work surface, wherein the first drawer housing defines an interior that holds at least one pull-out drawer; and a second drawer housing that is configured to be removably coupled beneath the first drawer housing defines an interior that holds at least one pull-out drawer.

15. A cart as in claim 14, wherein the first drawer housing and the second drawer housing are each configured to hold a pair of laterally spaced-part drawers.

16. A system, comprising:
a base;
a mast extending generally vertically up from the base;
a work surface operably coupled to the mast;
a computer comprising a controller; and
a computer monitor that is operably coupled to the controller, wherein the computer monitor is operably coupled to the mast so as to be positioned above the work surface;
a drawer system operably coupled to the mast so as to be disposed between the work surface and the base;
a battery removably coupled with the base and electrically coupled to the computer controller through the central mast; and
a solar charging system that has a solar power input that provides power to operate the computer.

17. A system as in claim 16, wherein said solar charging system includes a plurality of solar panels that are connected to said computer.

18. A system as in claim 16, wherein the drawer system comprises a first drawer housing that is configured to be removably coupled beneath the work surface, wherein the first drawer housing defines an interior that holds at least one pull-out drawer; and a second drawer housing that is configured to be removably coupled beneath the first drawer housing defines an interior that holds at least one pull-out drawer.

19. A system as in claim 18, wherein the first drawer housing and the second drawer housing are each configured to hold a pair of laterally spaced-part drawers.

20. A system as in claim 16, further comprising a central administrator that is operatively connected to said computer.

* * * * *